United States Patent [19]
Shanbrom

[11] Patent Number: 5,985,260
[45] Date of Patent: Nov. 16, 1999

[54] DISINFECTION OF BLOOD AND BIOLOGICALS WITH ACTIVE ALBUMIN-IODINE COMPLEX

[75] Inventor: Edward Shanbrom, Santa Ana, Calif.

[73] Assignee: Shanbrom Technologies, LLC, Ojai, Calif.

[21] Appl. No.: 08/529,650

[22] Filed: Sep. 18, 1995

[51] Int. Cl.$^6$ .......................... A61K 31/74; A01N 59/22; A01N 1/02
[52] U.S. Cl. ...................... 424/78.08; 424/667; 424/672; 435/2; 435/1.1
[58] Field of Search ............................. 424/28, 37, 78.08, 424/78.22, 667, 672; 435/1.1, 2

[56] References Cited

U.S. PATENT DOCUMENTS

| | | | |
|---|---|---|---|
| 4,368,081 | 1/1983 | Hata et al. | 134/2 |
| 4,442,037 | 4/1984 | Arakawa et al. | 260/397.2 |
| 4,749,570 | 6/1988 | Poznansky | 424/94.3 |
| 4,767,745 | 8/1988 | Young et al. | 514/21 |
| 4,923,677 | 5/1990 | Simon et al. | 422/37 |
| 5,008,106 | 4/1991 | Merianos et al. | 424/80 |
| 5,122,370 | 6/1992 | Merianos et al. | 424/78.05 |
| 5,185,371 | 2/1993 | Rubinstein | 422/28 |
| 5,360,605 | 11/1994 | Shanbrom | 424/78.08 |
| 5,370,869 | 12/1994 | Shanbrom | 424/78.22 |

FOREIGN PATENT DOCUMENTS

WO 93/17693  9/1993  European Pat. Off. .

OTHER PUBLICATIONS

Green, B. L. et al "The use of sodium sulfite as a neutralizer for evaluating povidone–iodine preparations" Helath Laboratory Science, vol. 11, No. 3, pp. 188–194, Jul. 1974.

F. Highsmith, et al., "Iodine–Mediated Inactivation of Lipid–and Nonlipid–Enveloped Viruses in Human Antithrombin II Concentrate", Blood, vol. 86, No. 2 (Jul. 15), 1995: pp. 791–796.

Waldemar Gottardi, et al., "The Decrease Of Efficiency Of Povidone–Iodine Preparations By Blood: Model Experiments On The Reaction Of Iodine Containing Disinfectants With Protein Constituents", Institute of Hygiene, University of Innsbruck, Austria pp. 357–371, 1985.

Jose L. Zamora, et al., "Inhibition of povidone–iodine's bactericidal activity by common organic substances: An experimental study", Surgery, vol. 28, No. 1, Jul. 1985, pp. 25–29.

*Primary Examiner*—Sheela Huff
*Assistant Examiner*—Yvonne Eyler
*Attorney, Agent, or Firm*—Graham & James LLP

[57] ABSTRACT

A method of disinfecting blood, blood components, biologicals, such as plasma, serum, cell concentrates, clotting proteins, etc., as well as tissues and organs for transplant comprising preparing and immediately adding active albumin-iodine complex to the material to be disinfected and thereafter using the disinfected material is disclosed. A modified blood bag for use with active albumin-iodine complex had a small satellite bag to contain albumin or active albumin-iodine complex and may also comprise a flow-through cartridge for preparing the active albumin-iodine complex.

14 Claims, 1 Drawing Sheet

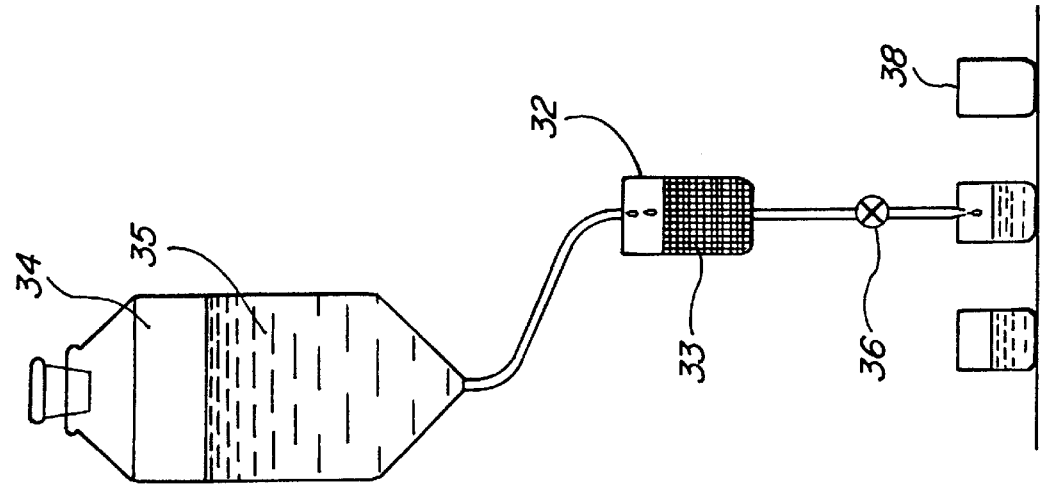
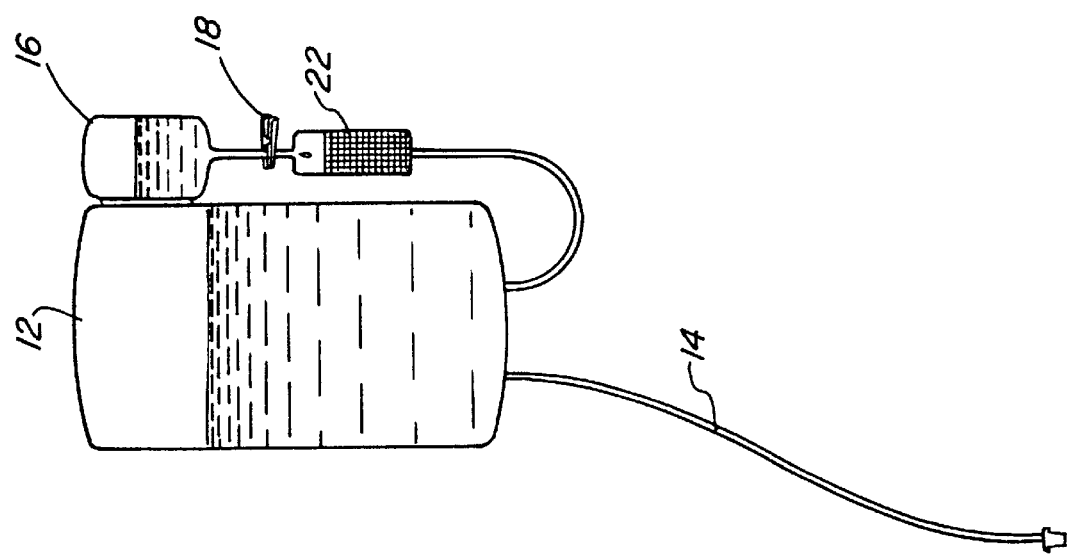

DISINFECTION OF BLOOD AND BIOLOGICALS WITH ACTIVE ALBUMIN-IODINE COMPLEX

BACKGROUND OF THE INVENTION

1. Field of the Invention

In general, the field of this invention lies in medicine and veterinary practice; most examples being related to the practice of medicine for the benefit of human patients, use in analogous fields of veterinary medicine to the extent applicable also being within the scope of the invention. More specifically, this invention relates to the treatment of blood and blood derivatives such as clotting factors, plasma, serum, platelets, packed red blood cells, and the treatment of other biologicals such as tissues, tissue cultures, cells, organs and products thereof to ensure freedom from disease-causing microbes.

2. Description of Related Art

The history of iodine as a disinfecting agent is long. Iodine was officially recognized by the Pharmacopeia of the United States in 1930, and clinicians and microbiologists have developed a great amount of experimental data on iodine as well as numerous clinical uses for iodine.

A number of authors have summarized the disinfecting properties of iodine and the other halogens by reviewing the literature and analyzing the existing data. Some of their most germane conclusions are:

(1) A standard destruction (i.e., a 99.999% kill in 10 minutes at 25° C.) of enteric bacteria, amoebic cysts, and enteric viruses requires available $I_2$ of about 0.2, 3.5, and 14.6 ppm, respectively.

(2) On a weight basis, iodine can inactivate viruses more completely than other halogens.

(3) In the presence of organic and inorganic nitrogenous substances, iodine is the cysticide of choice because it is not involved in side reactions that interfere with its disinfecting properties.

(4) $I_2$ is two to three times as cysticidal and six times as sporicidal as hydroiodic acid (HOI), while hydroiodic acid is at least 40 times as virucidal as $I_2$. This behavior is explained on the one hand by the higher diffusibility of molecular iodine through the cell walls of cysts and spores and on the other hand by the higher oxidizing power of hydroiodate.

Gottardi, *Iodine and Iodine Compounds* in DISINFECTION, STERILIZATION, AND PRESERVATION, Third Edition, Block, Ed., Lea & Febiger, Philadelphia, 1983, and the references cited therein provide more details respecting the background discussed above.

Although the exact means by which iodine exerts its disinfecting properties are not fully known, it can be assumed that the following chemical reactions are, to some extent, involved:

(1) iodine reacts with the basic amino group (N—H) that forms an essential part of amino acids and also forms N-iodo derivatives with the nitrogen in nucleotide bases; these reactions alter the charge structure as well as geometry (iodine is a very large atom) of proteins and other biomolecules, thereby disrupting their functions;

(2) iodine oxidizes sulfhydryl groups (S—H) of the amino acid cysteine, thereby disrupting the disulfide bridges that stabilize and determine secondary and tertiary structure of peptides and proteins;

(3) iodine reacts with the carbon-carbon double bond of unsaturated fatty acids, thereby altering or disrupting lipid bilayers and generally damaging biological membranes; and (4) iodine reacts avidly with the phenolic side chain of the amino acid tyrosine, further disrupting protein structure.

Despite the successes achieved with iodine, it has long been known that the use of iodine possesses a number of more or less serious drawbacks. Not only is iodine poisonous if ingested in quantity, it irritates and stains the skin and has a rather unpleasant odor. Because iodine causes considerable stinging if used to disinfect wounds and because there is significant danger of developing an allergic reaction to topical iodine applications, considerable effort has been expended to develop iodine compounds or complexes which preserve the disinfecting properties of iodine while suppressing its undesirable properties.

Iodine-polymer complexes, e.g. with polyvinylpyrrolidone (PVP) and complexes of iodine with nonionic surfactants, e.g. polyethylene glycol mono-(nonylphenyl)-ether, have been used with considerable success. However, use of these compounds in direct contact with fragile biological materials has been limited either because the killing power of iodine is dissipated in the biological material or because iodine damages the biological material.

Povidone iodine (iodine-PVP complex) is capable, under favorable circumstance, of killing all classes of pathogens encountered in human infection: both gram-positive and gram-negative bacteria, mycobacteria, fungi, yeasts, protozoa, and viruses. It has been assumed that these and similar instances of disinfection by iodine are mediated by the chemical reactions listed above.

Although damage to biological material during disinfection by iodine and iodine complexes is a serious problem, an equally serious problem is posed by the dissipation of the iodine by the biological material. That is, the very chemical reactions that result in disruption of microbes also occur between iodine and the biological materials being disinfected. Thus, iodine is consumed by proteinaceous substrates and its efficacy as a disinfectant is thereby reduced. This may be due to a reducing effect of the material to be disinfected which leads directly to the conversion of iodine into nonbacteriacidal iodide. Alternatively, free iodine may be consumed in the various organic reactions mentioned above. Thus, not only is the reservoir of available iodine diminished, but the equilibrium of triiodide may also be influenced as well since an increase of iodide results in more molecular iodine being converted into triiodide. This results in a decrease in the concentration of free molecular iodine, the actual antimicrobial agent.

On the other hand, when povidone-iodine preparations are mixed with liquid biological materials (e.g. blood, etc.) there is, in addition, a dilution effect characteristic of povidone-iodine systems which actually results in an increase in the equilibrium concentration of free molecular iodine. To what extent the latter effect compensates for the other two effects depends on the content of reducing substances.

When povidone-iodine is mixed with whole blood, a marked decrease in the concentration of free molecular iodine occurs, while, when mixed with blood plasma, the iodine concentration remains practically unchanged. Durmaz et al., *Mikrobiyol. Bul.* 22(3), abstract (1988); Gottardi, *Hyg. Med.* 12(4): 150–54 (1987). Presumably, the abundant proteins of the cellular constituents of blood are more reductive and contain many more iodine reactive sites than do the soluble proteins of the plasma. This result may be slightly at odds with the well known fact that albumin (a major plasma protein) is particularly effective in reducing or totally inhibiting the biocidal power of iodine.

The current inventor has explored the use of iodine complexes in the treatment of blood and blood complexes in considerable detail. For example, the inventor's U.S. Pat. No. 5,370,869 discloses a method of disinfecting platelet-bearing liquid by contacting the liquid to be cleansed with solid povidone-iodine to expose the platelet-bearing liquid to iodine and thus kill pathogenic organisms therein, and thereafter removing the liquid from contact with the solid povidone-iodine.

Additional aspects of the inventor's work are reported by Highsmith et al., *Blood,* 86(2): 791–96 (1995). This study explored the use of liquid iodine for inactivation of several lipid and nonlipid enveloped viruses in an antithrombin III (AT-III) concentrate. Iodine at levels of about 0.01% to about 0.02% caused between 43% and 94% loss of AT-III activity, as well as degradation of AT-III as shown by sodium dodecyl sulfate-polyacrylamide gel electrophoresis and Western blot analysis.

However, addition of up to about 0.1% human albumin protected the AT-III against both inactivation and fragmentation. At albumin levels sufficient to retain greater than 75% of AT-III activity, more than $1 \times 10^6$ sindbis, encephalomyocarditis, and vesicular stomatitis viruses, more than $1 \times 10^4$ of pseudorabies, and more than $1 \times 10^3$ of human immunodeficiency virus were inactivated. Except with sindbis virus, this represented complete inactivation of all the viruses spiked into the AT-III concentrate.

The numerous references cited in the above-identified patent and research publication, of which the present inventor is a coauthor, and which describes results of tests using his concepts and methods, provide in-depth discussions of the background technology, to which the reader is referred. These disclosures are incorporated herein by reference.

OBJECTS AND SUMMARY OF THE INVENTION

It is an object of the present invention to provide a means of applying the exceptional disinfection properties of iodine to blood or other biologicals while, at the same time, limiting the destructive action of the iodine upon the material to be disinfected;

It is a further object of the present invention to provide an effective carrier of iodine that can be added to blood or other biologicals without danger of inducing unwanted immunological reactions in a human recipient; and It is also an object of the present invention to provide a disinfecting iodine carrier that can be used on biologicals intended for cell culture and other nonhuman applications.

The current inventor discovered that, in spite of the known fact that albumin generally destroys the biocidal power of iodine, albumin, when reacted with sufficient iodine, forms a complex somewhat analogous to the previously-known iodophors such as povidone-iodine while maintaining significant advantages over povidone-iodine. The material is generally nontoxic, nonimmunogenic and disinfects with minimal damage to cell and tissues. A significant aspect of the discovery is that the albumin-iodine complex is "active," that is, capable of significant disinfectant action only for a relatively short period of time, minutes to days, after formation.

Although much of the iodine complexed with albumin is covalently bound, a significant portion of the iodine is available for contact and reaction with biological materials in an amount such that the active albumin-iodine complex in an aqueous solution possesses oxidizing iodine properties equivalent to at least about 0.0001 weight percent (weight of iodine/weight of albumin). However, as time passes, the active complex becomes deactivated, losing its oxidizing iodine properties as the iodine becomes reduced and/or undergoes further covalent reaction with the albumin. Thus, time may be of the essence in the preparation and use of the active albumin-iodine complex of the present invention.

The invention thus encompasses a process of preparing albumin-iodine comprising reacting substantially pure albumin, preferably unsterilized, unstabilized, and delipidated, with sufficient iodine-containing reagent to substantially saturate all binding sites thereon. Albumin-iodine complex is useful in most processes in which povidone-iodine can be used. In general, a liquid composition that contains bacteria, virus, or other pathogenic organisms can be sterilized by bringing it into contact with albumin-iodine complex. Thereafter, if it is desired to assure total iodine removal, the solution can be brought into contact with an iodine absorbing agent or a reducing agent such as a reducing sugar, ascorbate, sulfite, etc. may be added to eliminate the last traces of oxidizing iodine.

The invention is embodied, inter alia, in a method of disinfecting biological materials. The steps of the method include forming the active albumin-iodine complex, treating biological material before or after separation of the components thereof with the active albumin-iodine complex to provide activity equivalent to a concentration of about 0.01 weight percent to about 1 weight percent iodine (resulting from the addition of oxidizing iodine to albumin in the formation of albumin-iodine complex) in said material before separation of the components thereof.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

FIG. 1 depicts, largely schematically, an improved blood bag system well suited to the practice of the present invention on blood and blood fraction; and FIG. 2 depicts, largely schematically, a device for using the present invention to disinfect aliquots of biologicals prior to lyophilization.

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide for the preparation and use of an active albumin-iodine complex.

The risks of infection from blood fractions or blood products are well known. One of the great tragedies of modern medicine is the infection of many patients, most frequently hemophiliacs who require frequent blood transfusions or infusion of blood products to normalize clotting, with HIV (Human Immunodeficiency Virus). The purification of the nation's and the world's blood and blood products for transfusion would constitute a monumental step forward in the history of medicine. The risks of infection from red blood cell concentrates is similar to comparable risks associated with whole blood.

Besides HIV risks, hazards of contamination of blood, plasma fractions and other biologicals, including transplanted tissues and organs, by one of the numerous types of viral hepatitis continue to exist, and precautions must be taken to minimize these risks. Indeed, the major hazard in producing fractions from large pools of plasma is the transmission of hepatitis and other virus. This is a danger both for the recipient of the fractions and for the workers in fractionation plants. It has been shown that fractionation workers, particularly those engaged in the preparation of plasma pools, are at high risk of developing hepatitis B which disease is strongly correlated with later development of liver cancer.

The present invention involves a special use of albumin. Human serum albumin is a remarkable protein which performs numerous tasks critical to maintenance of the milieu intèrieur. The best known functions of albumin involve regulation of transvascular fluid flux and, hence, intra and extravascular fluid volumes and also transport of lipid and lipid-soluble substances. However, it is also involved in a number of other vital functions, some of which have only recently been suggested, and perhaps others which are as yet unrecognized.

Among recognized unique features of albumin are: (a) binding and, hence, inactivation of toxic products; (b) regulation of the plasma and interstitial fluid concentrations of endogenous and exogenously administered substances and drugs; (c) involvement in anticoagulation; (d) maintenance of microvascular permeability to protein; and (3) scavenging of free radicals and prevention of lipid peroxidation. See, UNIQUE FEATURES OF ALBUMIN: A BRIEF REVIEW, Thomas E. Emerson, Jr., Ph.D., *Critical Care Medicine*, Vol. 17, No. 7 (1989).

An important feature which segregates albumin from other colloids as well as crystalloids is its unique ability to bind reversibly with both anions and cations; hence, albumin can transport a number of substances including fatty acids, hormones, enzymes, dyes, trace metals, and drugs. Substances which are toxic in the unbound or free state are generally not toxic when bound to albumin. This binding property also enables albumin to regulate the extracellular concentration of numerous endogenous as well as exogenously administered substances.

Albumin in general has three types of binding sites (one for acidic, one for basic, and one for neutral compounds), and it plays a critical role in the binding and transport of lipid and lipid-soluble material. Some of these sites could well be involved in iodine binding in active albumin-iodine complexes and may explain why albumin proves an especially effective iodine-carrying agent.

Albumin is already added to many biologicals to improve stability, often in amounts of about 0.1 weight percent. For lyophilized products albumin is often added in amounts of about 1 weight percent. In the case of protein biologicals, such as coagulation factors, the major function of added albumin is probably to provide "background" protein to help protect the coagulation factor from denaturation. Other soluble proteins might also serve but albumin is readily available, extremely soluble and nonimmunogenic. In the case of cells and cellular fractions albumin has probably been selected through evolution to provide protection to and stability for cellular structures. In the case of tissue culture products albumins (bovine serum albumin in many cases) act as growth factors and may be essential for optimal cell growth. In any case, cell and protein protective action as well as nonimmunogenicity all mitigate towards the use of albumin as the additive of choice.

The active albumin-iodine complex of the present invention is prepared beginning with substantially pure albumin. The albumin may have traces of other proteins and biological materials, of course, and term "pure" is used in the sense common in reference to biological isolates that inherently contain some biologicals in addition to the principal constituent. The degree of purity required is dependent upon the intended use of the final product, and the presence of trace amounts of other materials is not per se detrimental to the present invention.

Nondenatured, nonpasteurized albumin free of stabilizers such as caprylate and fatty acids, etc., is preferred. Indeed, the time consuming and expensive steps of killing microbes which are required in the normal preparation of albumin is essentially surplus or irrelevant, since all microbes will be killed by the iodine. Iodine in any form may be reacted with the albumin using any convenient technique or apparatus. It is possible to form active albumin iodine complex by adding an iodine solution to an albumin solution. It is even possible to add liquid iodine directly to an albumin containing solution of a material to be disinfected. However, in both cases one usually has an excess of free iodine in the solution. In the second case, the free iodine may damage the material to be disinfected despite the protective action of the albumin.

Therefore, it has been found convenient to use an insoluble iodine donating material such as cross-linked povidone-iodine as the iodine source because this material provides a convenient source of iodine, has high iodine content, and does not add other chemicals or constituents to the resulting albumin-iodine. Alternatively, other insoluble iodine binding agents such as starch, polyvinyl acetate copolymer (vinyl-acetate-alcohol-acetate copolymer, a reaction product of formaldehyde and polyvinyl alcohol) or even cross-linked albumin or other protein may be used. The general goal is to rapidly saturate albumin with iodine without adding a significant amount of free soluble iodine. Preferably, a solution of albumin is passed through a bed or column of a solid, insoluble iodine source where it becomes approximately saturated with iodine.

Observations during formation of active albumin-iodine complex leads to the conclusion that there are, generally, two sets of binding sites on albumin, one of which binds iodine virtually irreversibly (probably by covalent reaction), and one of which holds the iodine more reversibly, and apparently more on the surface of the molecule. It is not suggested, however, that all binding sites within one of the general types are the same, as it is known that albumin has many binding sites presumably having a great diversity of binding strength for various molecules.

The term "active albumin-iodine complex," therefore, represents albumin in which virtually all of the irreversible iodine binding sites have been filled and in which a majority, approximately, of the reversible binding sites have iodine bound thereto. It is hypothesized that the so-called reversible sites are responsible for the advantageous properties of the active albumin-iodine complex. To some extent these sites may actually release molecular iodine for reaction with microbes, etc. However, simple release does not explain the unusual protective properties of the complex.

It seems likely that the sites that hold active iodine are accessible to microbes, etc. when they physically come into contact with the albumin molecules. Apparently, the active albumin-iodine complex is not as effective in delivering "killing" iodine to blood cells and other biologicals so that these desirable components are spared from iodine damage. Perhaps some type of steric hinderance generally prevents blood cells and other biologicals from directly contacting the active iodine sequestered within the albumin.

The active complex does not remain active indefinitely. Therefore, it is preferred to mix the active albumin-iodine complex with the material to be disinfected within five minutes or so of the preparation of the complex. The complex immediately begins to loose strength, probably as the active, reversibly bound iodine becomes covalently bound to the albumin. It is known that the complex retains at least some activity for at least about one day after preparation. However, it will be apparent that reproducible results require using the complex relatively soon after preparation. Within a few days or less of preparation the active albumin iodine complex will have completely lost its disinfectant properties.

A preferred method is to use active albumin-iodine complex that is freshly prepared and is added in an amount from about 0.01 weight percent to about 1 weight percent iodine based on the weight of the cell containing composition (weight of iodine/weight of composition to be treated). Generally, albumin will covalently bind at least about 0.01 weight percent iodine. Much of the iodine in excess of this amount will be available for disinfectant purposes. Generally, a concentration of iodine at 1 weight percent is more than enough to kill or inactivate any known microbes.

The albumin-iodine complex is allowed to remain in contact with the blood cells or plasma, or other biological material being disinfected for a period of time to kill the microbes, but not for long enough to denature or otherwise injure the biological material. Generally, the use of active albumin-iodine complex will spare the disinfected biological material from iodine induced damage. This means that it is usually not necessary to take steps to reduce or otherwise inactivate the iodine albumin.

It may be somewhat difficult to predict the minimum contact time to cause adequate disinfection. While in some uses a minimum contact time of under an hour is preferred, it appears that in many instances several hours' contact, at least, is necessary to ensure adequate disinfection. That is, complete disinfection as caused by the active albumin-iodine complex is frequently more time consuming that disinfection with traditional iodine sources. This is in keeping with the above-explained theory that little free iodine is available. If the disinfection process requires collisions with or binding to albumin-iodine molecules, the process will necessarily be slower because of the greater mass and the lower absolute concentration of albumin molecules as compared to traditional iodine-based disinfectant.

After several hours or tens of hours the active complex loses its activity (probably through internal iodine-albumin reactions) and is no longer capable of causing either iodine-induced damage to biological material or iodine-killing of infectious agents. However, if the biological material to be treated is especially labile, after passage of sufficient time to effect disinfection, a reducing agent can be added in an amount to reduce substantially all remaining active iodine, thus preventing any iodine further induced damage. As far as is known, albumin-iodine complex largely retains its favorable biological protective qualities so that after the active iodine has dissipated the spent albumin-iodine complex is harmless or even beneficial.

As a method of disinfecting blood derivatives, the invention may comprise treating blood before separation of the components thereof with active albumin-iodine complex sufficient to provide iodine equivalent from about 0.01 weight percent to about 1 weight percent iodine based on the weight of the material to be treated. Generally, the presence of whole cells increases the amount of iodine needed by at least four fold. Following disinfection the blood may then be fractionated. Thereafter the blood derivative can be treated by addition of a physiologically-acceptable reducing agent to remove residual iodine. Alternatively, the disinfected blood can be treated with the reducing agent before fractionation.

In general a solution of reducing agent, e.g. a reducing sugar (or mixtures of reducing sugars), ascorbic acid or ascorbate, a sulfite, e.g. sodium sulfite, etc. in which the agent is in a concentration of about 0.001 to about 1 percent is suitable and such is implicit unless otherwise noted. However, it should be noted that in most cases the active albumin-iodine complex will naturally lose activity making use of the reducing agent unnecessary.

FIG. 1 depicts, schematically, a portion of a blood bag system of the type commonly in use, comprising a bag 12 and interconnecting conduit tubing 14 for collecting blood prior to separating the blood into various constituents and adding preservatives, etc. to the blood. Included in this bag system is a satellite bag 16 connected to the main blood bag 12 by means of tubing 18. The satellite bag 16 is shown as an integral part of the main bag 12; however, the exact location of the satellite bag 16 will depend on the chosen design and manufacturing method. Connected in line with the tubing 18 is an iodination cartridge 22.

In one configuration, the satellite bag 16 contains an aqueous solution of human serum albumin. Physiologically-acceptable preservatives as may be necessary to ensure stability and freedom from viable microorganisms may be included in the albumin solution. The amount and volume of albumin solution is selected to cause negligible dilution when added to the main blood bag 12 when this is filled with collected blood (about one liter) or blood fractions to be disinfected.

The iodination cartridge 22 comprises an insoluble source of oxidizing iodine such as discussed above. If suitable materials and reliable solid particle barriers are used, a very small amount of crystalline iodine could be used. This approach, however, presents manufacturing and storage difficulties that need not be faced if an insoluble iodine donor is used as the source of iodine. Also, by using an insoluble iodine-binding material to deliver iodine to the albumin very little, if any, free iodine is ever present.

In carrying out the process, the blood, plasma, serum, packed cells, or biological blood constituent is introduced into the main blood bag 12 through the tubing 14. The albumin solution, contained in the satellite bag 16, is allowed to flow through the iodination cartridge 22 by opening a clamp valve 24. In the iodination cartridge 22 the albumin solution adsorbs and/or absorbs iodine to form active albumin-iodine complex. This freshly-prepared active albumin-iodine complex flows directly from the cartridge 22 into the bag 12, where it is mixed with the blood or blood constituent. The oxidizing iodine content of the active albumin-iodine complex is maximally active in the freshly-prepared complex and effectively kills or inactivates viruses, bacteria, and other microorganisms in the blood or other constituent of the main blood bag 12. At the same time, the albumin helps protect cells from lysis and reduces the inactivation or denaturation of blood clotting factors and other labile biochemicals.

As mentioned above, the active albumin-iodine complex loses activity over time and reverts to a substance that acts essentially like ordinary albumin. However, it is possible that the active complex may damage labile biologicals or cellular materials. This problem may be solved by introducing a volume of a biologically acceptable reducing agent into the main blood bag 12 to neutralize the iodine before appreciable damage is caused.

However, in many cases adjustment to the amount of albumin and the extent of iodination of that albumin will prevent damage. That is, depending on the exact biological material to be treated the amount of iodine in the iodination cartridge 22 and the amount of albumin in the satellite bag 16 can be adjusted to prevent over iodination of and consequent damage to the biological target material. Providing a quantity of albumin solution at a higher albumin concentration to a fixed quantity of iodine releasing material will result in an active albumin-iodine complex with a lower amount of active iodine and, hence, less of a tendency to cause damage. Alternatively, the total amount of iodine available in the iodination cartridge 22 can be reduced. The determination of optimum conditions is obvious to one of ordinary skill and needs to be carried out only initially as each different type of biological is used with the present invention.

Since the relative relationship between the quantity and volume of albumin and the quantity of free iodine available in the cartridge 22 can be critical, an alternative method of packaging the components may be advantageous. The satellite bag 16 may contain a premeasured quantity of lyophilized albumin to which is added, just before use, a premeasured volume of sterile diluent (possibly with a syringe). After gentle mixing to dissolve the albumin, the albumin solution is allowed to flow through the iodination cartridge 22 as described above. The advantage of this configuration is that the blood bag system need contain no liquid. This improves storage and eliminates the need for a preservative in the albumin solution.

It has also been discovered that if freshly prepared active albumin-iodine complex is rapidly lyophilized, the dried product still has considerable disinfectant ability when later reconstituted. It appears that lyophilized active albumin-iodine complex can be used in the above-explained device thereby eliminating the need for the iodination cartridge 22. However, it is not yet know if the lyophilized material retains sufficient activity for all purposes. Also, the long term stability of the lyophilized material has not yet been determined. It is possible that activity will continue to decay even after the complex has been lyophilized. It is also possible that the lyophilized complex will become insoluble with time.

FIG. 2 shows a related device for the preparation of active albumin-iodine complex to be used to disinfect purified or semipurified fractions or biologicals which can be stored lyophilized in a dry form. In this case it is preferred to add a small aliquot of active complex to each vial prior to lyophilization. For this purpose a large iodination cartridge 32 is provided. This cartridge is substantially a giant version of the iodination cartridge 22 used with the blood bag system and contains a quantity of insoluble iodine donor material 33.

A source 34 of albumin solution 35 is arranged to flow by gravity through the large cartridge 32. Alternatively, a pump (not illustrated), such as a peristaltic pump, can be arranged to pump the albumin solution through the cartridge 32. The active albumin iodine complex thus formed is immediately metered through a valve 36 into lyophilization vials 38 containing the biological to be disinfected. The liquid is mixed and allowed to incubate for a predetermined time before the vials 38 are frozen as a prelude to freeze drying. Although a reducing agent can be used to neutralize any remaining active iodine, free iodine is volatile and is removed by the lyophilization process.

Of course, several alternatives are possible to the above described process. A lyophilized source of active albumin-iodine complex may be used. Rather than adding the active complex to individual vials, the biological material can be disinfected in bulk prior to being dispensed into vials. It is even possible to disinfect the starting materials for the entire biological fractionation process. The problem with some of these alternatives is that all subsequent steps should then be carried out under antiseptic conditions to prevent recontamination of the disinfected material.

In many biochemical procedures a final product is eluted from a chromatography column. In those cases it is common to use an albumin solution to prefill tubes of a fraction collector that receives the eluate to provide protection from denaturation. It is simple to substitute active albumin-iodine complex for some or all of the protective albumin prefill. The precise procedure adopted will depend, of course, on the volumes and nature of the materials being worked with.

In the case of organs or tissues such as those used in transplants, these biological materials can be disinfected by being bathed or soaked in a bath containing active albumin-iodine complex from any of the sources discussed above. This type of treatment works particularly well with relatively thin objects such as skin explants or corneas. In the case of larger organs it is often possible to perfuse the organs with a solution of the active complex in a biologically compatible solution such as a Ringer's solution. It is also possible to add oxygen carrying materials such as perfluorocarbons or employ a hyperbaric system to ensure that the organ is properly oxygenated. Perfusion is effective to eliminate many infectious agents. Obviously viruses that are actually incorporated into and replicating within the cells of the organ will escape the iodine treatment.

Throughout this discussion reference has been made to the nonimmunogenic and protective effects of albumin. One of ordinary skill in the art will recognize that the type of albumin must be changed depending on the application. That is, while human albumin is nonimmunogenic in humans and is ideally suited to protect human cells and tissues, human albumin would be immunogenic to another species such as a goat or rabbit. Thus, when the present invention is used with animal blood products, etc. as in veterinary medicine, the albumin should be selected to match the recipient species. In the same way when the present product is used with biologicals such as vaccines, care must be taken to properly match the albumin to the ultimate recipient species.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A method of disinfecting a biological sample, said sample being selected from the group consisting of blood, blood derivatives, clotting factors, plasma, serum, platelets, packed red blood cells, tissues, tissue cultures, cells and organs, comprising the steps of adding albumin-iodine complex to the sample wherein said albumin-iodine complex is used within one hour after formation of the said complex, mixing the sample with said complex, and allowing a resulting mixture to react.

2. The method of claim 1, wherein the albumin-iodine complex is prepared by reacting an albumin solution with an insoluble iodine containing material and removing said material from the resulting solution.

3. The method of claim 2, wherein the insoluble iodine containing material comprises a matrix material to which iodine has been added, the matrix material being selected from the group consisting of insoluble polyvinylpyrrolidone, insoluble starch, insoluble protein, and polyvinyl acetate copolymer.

4. The method of claim 1, wherein the albumin-iodine complex is added in an amount to provide from about 0.01 weight percent to about 1 weight percent iodine, based on the weight of the biological sample to be treated.

5. The method of claim 1, wherein a reducing agent is added to said mixture after the albumin-iodine complex has reacted.

6. The method of claim 5, wherein the reducing agent is selected from the group consisting of reducing sugars, ascorbate, and sulfite.

7. A method of disinfecting a biological sample said sample being selected from the group consisting of blood, blood derivatives, clotting factors, plasma, serum, platelets, packed red blood cells, tissues, tissue cultures, cells and organs, comprising the steps of preparing albumin-iodine complex by passing dissolved albumin through an insoluble iodine containing material, wherein said albumin-iodine complex is used within one hour of preparation, adding said albumin-iodine complex to the protein-containing solution in an amount to provide from about 0.01 weight percent to about 1 weight percent iodine, based on the weight of the biological sample to be treated, and completely mixing said complex with the said sample.

8. The method of claim 7, wherein the insoluble iodine containing material comprises an insoluble matrix material to which iodine has been added, the matrix material being selected from the group consisting of insoluble polyvinylpyrrolidone, insoluble starch, insoluble protein, and polyvinyl acetate copolymer.

9. The method of claim 7, wherein a reducing agent is added to the resulting mixture.

10. The method of claim 9, wherein the reducing agent is selected from the group consisting of reducing sugars, ascorbate, and sulfite.

11. A method of disinfecting tissues and organs before transplant comprising the steps of preparing albumin-iodine complex by passing dissolved albumin through an insoluble iodine containing material, wherein the resulting albumin-iodine complex is used within one hour of preparation and adding said albumin-iodine complex to a solution which is used to bathe or perfuse the tissues and organs in an amount to provide from about 0.01 weight percent to about 1 weight percent iodine, based on the weight of the solution.

12. The method of claim 11, wherein the insoluble iodine containing material comprises an insoluble matrix material to which iodine has been added, the matrix material being selected from the group consisting of insoluble polyvinylpyrrolidone, insoluble starch, insoluble protein, and polyvinyl acetate copolymer.

13. The method of claim 11, wherein a reducing agent is added to the tissues and organs after the albumin-iodine complex has been added.

14. The method of claim 13, wherein the reducing agent is selected from the group consisting of reducing sugars, ascorbate, and sulfite.

* * * * *